(12) United States Patent
Bartsch

(10) Patent No.: US 6,936,444 B1
(45) Date of Patent: Aug. 30, 2005

(54) PROCESS FOR THE PREPARATION OF L-PHOSPHINOTHRICINE BY ENZYMATIC TRANSAMINATION WITH ASPARTATE

(75) Inventor: Klaus Bartsch, Königstein (DE)

(73) Assignee: Aventis CropScience GmbH, Frankfurt (DE)

(*) Notice: Subject to any disclaimer, the term of this patent is extended or adjusted under 35 U.S.C. 154(b) by 0 days.

(21) Appl. No.: 10/018,331

(22) PCT Filed: Jun. 30, 2000

(86) PCT No.: PCT/EP00/02809

§ 371 (c)(1),
(2), (4) Date: May 10, 2002

(87) PCT Pub. No.: WO00/66760

PCT Pub. Date: Nov. 9, 2000

(30) Foreign Application Priority Data

Apr. 30, 1999 (DE) .................................. 199 19 848

(51) Int. Cl.⁷ ............................................. C12P 13/04
(52) U.S. Cl. ....................................... 435/106; 435/128
(58) Field of Search ................................ 435/128, 106

(56) References Cited

U.S. PATENT DOCUMENTS

| 4,826,766 A | 5/1989 | Rozzell |
| 5,221,737 A | 6/1993 | Bartsch et al. |
| 6,335,186 B1 * | 1/2002 | Bartsch et al. ............... 435/128 |

FOREIGN PATENT DOCUMENTS

| DE | 2717440 | 12/1977 |
| DE | 2856260 | 7/1979 |
| DE | 3750523 | 2/1995 |
| EP | 135846 | 4/1985 |
| EP | 248357 A2 | 12/1987 |
| EP | 249188 A2 | 12/1987 |
| EP | 249188 A3 | 1/1989 |
| EP | 344683 | 12/1989 |
| EP | 349965 | 1/1990 |
| EP | 477902 | 4/1992 |
| EP | 248357 B1 | 7/1993 |
| WO | 98/53088 | 11/1998 |

OTHER PUBLICATIONS

Bartsch, et al., "Stereospecific production of the herbicide phosphinothricin (glufosinate): purification of aspartate transaminase from *Bacillus stearothermophilus*, cloning of the corresponding gene, aspC, and application in a coupled transaminase process," Appl. Environ. Microbiol., Oct. 1996, vol. 62 No. 10 pp. 3794-3799.

Fotheringham, et al., "Biocatalytic production of unnatural amino acids, mono esters and N-protected derivatives," Chimica Oggi/Chemistry Today, Sep./Oct. 1997, pp. 33-37.

Taylor, et al., "Novel biosynthetic approaches to the production of unnatural amino acids using transaminases," Tibtech, Oct. 1998, vol. 16, pp. 412-418.

* cited by examiner

Primary Examiner—Herbert J. Lilling
(74) Attorney, Agent, or Firm—Frommer Lawrence & Haug LLP

(57) ABSTRACT

The patent application describes a process for the enzymatic chiral synthesis of L-phosphinothricin by transamination from its corresponding keto acid PPO with aspartate as amino donor. It is possible by a suitable reaction procedure to achieve a quantitative conversion on use of approximately equimolar amounts of amino donor and acceptor with complete consumption of the donor amino acid aspartate. The use of thermally stable transaminases makes a higher reaction rate and correspondingly large space/time yields possible.

9 Claims, No Drawings

PROCESS FOR THE PREPARATION OF L-PHOSPHINOTHRICINE BY ENZYMATIC TRANSAMINATION WITH ASPARTATE

The invention relates to the technical area of the synthesis of crop protection agents, in particular the synthesis of L-2-amino-4-(hydroxymethylphosphinyl)butyric acid (L-phosphinothricin, L-PPT) from 4-(hydroxymethylphosphinyl)-2-oxobutyric acid (HMPB, PPO) by enzymatic transamination in the presence of asparate in the presence of a PPO-specific aspartate transaminase (Asp-TA). The compound L-PPT, its salts and some derivatives thereof are herbicidal reactive non-proteinogenic amino acids or salts and derivatives thereof (DE-A-2717440). The L form in each case is biologically active whereas the D form in each case is virtually inactive (DE-A-2856260).

It has previously been disclosed that transaminases are particularly suitable, because of their high stereo selectivity and their relatively broad substrate specificity, in particular for the chiral enzymatic synthesis of amino acids from their corresponding keto acid precursors. One disadvantage for the industrial use of transaminases is, however, their equilibrium constant of about 1, so that only a 50% yield of the required product can generally be obtained (U.S. Pat. No. 4,826,766). EP-A-0344683 and U.S. Pat. No. 5,221,737 describe the preparation of the herbicidal agent L-phosphinothricin [(L-homoalanin-4-yl(methyl)phosphinic acid, L-2-amino-4-(hydroxymethylphosphinyl)butyric acid, L-PPT)], a non-proteinogenic amino acid, by transamination from the corresponding keto acid [(2-oxo-4-(hydroxy)(methyl)phosphinoyl)butyric acid, PPO)] with 4-amino-butyrate: 2-ketoglutarate transaminase (GABA transaminase, EC 2.6.1.19) from *Escherichia coli*. Quantitative conversion requires a large molar excess of the amino donor glutamate, which makes purification of the reaction product difficult.

One solution of this problem is possible by use of aspartate as amino donor, because the corresponding keto acid oxaloacetate is unstable in aqueous medium and spontaneously decarboxylates to pyruvate. Removal of one reaction product from the equilibrium makes back-reaction impossible and quantitative conversion is possible even on equimolar use of keto acid and donor amino acid. A process of this type is described, for example, in EP-A-0135846.

However, application of this principle to the enzymatic synthesis of L-phosphinothricin has not to date been possible because the described GABA transaminase does not accept aspartate as amino donor, nor was any other transaminase with joint specificity for L-phosphinothricin and aspartate known.

As an alternative, a coupled 2-enzyme system consisting of PPT-specific transaminase and glutamate:oxaloacetate transaminase (GOT, EC 2.6.1.1) has been proposed (EP-A-0249188 and EP-A-0477902). In this reaction procedure, the glutamate used in the synthesis of L-PPT is regenerated from aspartate by means of GOT. The aspartate transaminase itself has no specificity for L-PPT/PPO. The spontaneous conversion of oxaloacetate into pyruvate also leads to a shift in the equilibrium in the direction of L-PPT synthesis for the overall reaction. In this case, quantitative product yields are possible on equimolar use of PPO and aspartate with distinctly less than an equimolar quantity of glutamate.

This coupled enzyme process makes it possible to reduce distinctly the overdosage of the donor amino acids present in the substrate solution compared with the acceptor keto acid PPO, which simplifies work-up of the product solution. However, it is still necessary in the coupled reaction procedure to use glutamate which—in equilibrium with ketoglutarate—remains in the reaction product or must be removed by elaborate purification processes from the structurally very similar amino acid L-PPT. In addition, optimization of the reaction procedure is more difficult with 2 enzymes than with one enzyme because of the different kinetic parameters.

Although previously disclosed aspartate transaminases such as, for example, GOT show no conversion of PPO, aspartate transaminases from microorganisms which likewise accept L-PPT/PPO with high specificity as substrate have now surprisingly been found. These enzymes catalyze direct transfer of the alpha-amino group of aspartate to PPO.

The present invention therefore relates to a process for the preparation of L-2-amino-4-(hydroxymethylphosphinyl)butyric acid (L-phosphinothricin, L-PPT) of the formula (I), its derivatives and/or salts,

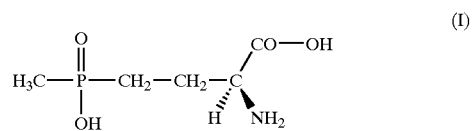

from 4-(hydroxymethylphosphinyl)-2-oxobutyric acid (HMPB, PPO) of the formula (II)

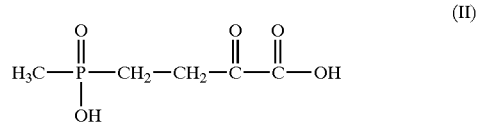

its derivatives and/or salts as acceptor by enzymatic transamination in the presence of aspartate as donor, the transamination taking place in the presence of one or more acceptor-specific, preferably PPO-specific, aspartate transaminases (Asp-TA) to give oxaloacetate and the compound of the formula (I), its derivatives and/or salts, preferably in the presence of one or more thermally stable and/or isolated aspartate transaminase and very particularly preferably in the presence of one or more aspartate transaminases with minimal substrate specificity for pyruvate, so that formation of the by-product alanine can be reduced or substantially avoided.

Salts of L-PPT are generally salts with inorganic and/or organic acids or mono- and disalts with inorganic and/or organic bases. Salts with acids (acid addition salts) are, for example, salts with mineral acids such as hydrochloric acid (hydrochloride) or sulfuric acid (sulfates), or with carbonic acid (carbonates, hydrogen carbonates) or with organic acids such as acetic acid (acetates), formic acid (formates), propionic acid (propiates) or tartaric acid (tartrates). Salts with bases are, for example, alkali metal and alkaline earth metal salts, ammonium salts, salts with organic amines such as primary, secondary or tertiary amines, and quaternary ammonium salts.

Derivatives are, for example, esters of L-PPT which are esterified on the phosphinic acid group, for example esterified with $C_1$–$C_{12}$-alkanols such as methanol, ethanol, n-propanol, i-propanol, n-, i- and sec- or tert-butanol and $C_3$–$C_6$-cycloalkanols such as cyclohexanol. Derivatives are also esters of L-PPT which are alternatively or additionally esterified on the carboxylic acid group, for example with the aforementioned alcohols. Derivatives are also the carboxamide of L-PPT and its derivatives, where appropriate N-alkyl or N,N-dialkylamides with, preferably, 1 to 4 C atoms in the alkyl moiety.

Derivatives of PPO are, for example, its salts with inorganic and/or organic bases, and bases suitable therefor have already been mentioned in connection with L-PPT. Derivatives are, for example, also esters of PPO which are esterified on the carboxylic acid group or the phosphinic acid group or both. Alcohols suitable for the ester groups are formally the alcohols suitable for esters of L-PPT, preferably the alkanols mentioned there. Derivatives are also the carboxamide of PPO and its derivatives which are esterified on the phosphinic acid group, and, where appropriate, corresponding N-alkyl or N,N-dialkylamides.

Aspartate preferably designates L-aspartic acid or its salts, preferably alkali metal salts. However, it is also possible to employ mixtures of L-aspartic acid with D-aspartic acid, for example racemic D,L-aspartic acid, as aspartate.

An alternative possibility in the process of the invention is to remove pyruvate which is present where appropriate in the reaction mixture by physical, chemical and/or enzymatic means, preferably by conversion by means of enzymatic catalysis, for example by acetolactate synthase (ALS), pyruvate decarboxylase, pyruvate oxidase, in particular acetolactate synthase; the conversion of pyruvate very particularly preferably takes place in the presence of a relatively thermally stable enzyme. The enzymes used thus can be in immobilized form where appropriate.

Both substrates (donor and acceptor) are employed for example in a molar ratio of 0.5–2:1 (based on L-aspartic acid:PPO), preferably 0.75–1.5:1, in particular approximately equimolar. On use of mixtures of L- and D-aspartic acids (salts), the molar quantity of L-aspartic acid (salt) is decisive. PPO derivatives must be employed in molar quantities equivalent to PPO. The presence of glutamate in the substrate solution is unnecessary. Some of the enzymes found exhibit excellent thermal stability. The process can therefore be carried out in a wide temperature range, for example at temperatures from 10 to 95° C., preferably from 40 to 90° C., in particular from 60 to 85° C. The preferred temperature range for enzymes which display no particular thermal stability is from 20 to 70° C., in particular from 30 to 40° C.

The relatively high temperatures allow the reaction rate to be considerably speeded up, which also makes it possible for more concentrated substrate solutions (10% strength) to be converted with high space/time yields. The reaction preferably takes place at a pH in the range from 6.5–10, preferably from 7 to 9, in particular from 7.5 to 8.5 in an appropriately suitable buffer system with a pKa in the range from 7–9, inter alia phosphate or tris buffer. Surprisingly, the enzymes which have been biochemically characterized in detail have no specificity for GABA and thus differ distinctly from previously disclosed L-PPT/PPO-specific transaminases.

Particularly high conversion rates can be achieved in the reaction if the formation of alanine during the transamination can be avoided or minimized. It is possible to use for this purpose where appropriate optimized ASP-TA variants without substrate specificity for pyruvate. An alternative possibility is for pyruvate to be removed physically, for example by use of selectively permeable membranes and/or chemically or enzymatically, for example by conversion with pyruvate decarboxylase, pyruvate oxidase or acetolactate synthase, from the reaction mixture (see, for example, Taylor et al., TIBTECH (1998), vol. 16, 412–418; Fotheringham et al., CHIMICA OGGI/chemistry today (1997), 9/10, 33–38; WO 98/53088).

Purification of the product, L-PPT, from the reaction solution can take place where appropriate by known and conventional processes, for example by extraction with methyl isobutyl ketone or by a cation exchange chromatography, for example with Amberlite® IR 120 (manufactured by Sigma).

The process of the invention is explained further in the following examples and the invention is defined in the patent claims. The following examples are not to be understood as limiting in this regard.

EXAMPLES

1.) Isolation of Soil Microorganisms with L-PPT-Specific Aspartate Transaminase Activity:

1 g of each of various soil samples (humus, loam, sand/Schwanheimer Düne, Frankfurt) were extracted with 10 ml of 10 mM Na phosphate buffer, pH=7.0, at room temperature for 1 h. Enrichment cultures in the following medium were inoculated from the extracts:

5 mM glucose
5 mM succinate
10 mM glycerol
10 mM PPO
10 mM L-aspartic acid
50 ml/l solution A
25 ml/l solution B
Solution A: 50 g/l $K_2HPO_4$
Solution B:
   2.5 g/l $MgSO_4$
   0.5 g/l NaCl
   25 ml/l from a stock solution containing:
      1 g/l $FeSO_4 \times 7H_2O$
      0.22 g/l $MnSO_4 \times H_2O$
      0.1 g/l $H_3BO_3$
      0.1 g/l $Na_2 MoO_4 \times 2H_2O$
      0.18 g/l $ZnSO_4 \times 7H_2O$
      0.16 g/l $CuSO_4 \times 5H_2O$
      0.1 g/l $CoCl_2 \times 6H_2O$
      1 ml/l 1 N HCl The cultures were incubated at 28° C. and 200 rpm on a shaker for 3–5 days. Enrichment of microorganisms able to grow with L-aspartic acid as sole N source was possible from one of the soil samples tested (humus). The culture was passaged further in the same medium several times and then plated out on agar medium of the same composition to isolate single clones. After incubation at 28° C. for 3–5 days, a total of 100 single colonies was isolated and again inoculated in liquid medium (see above). The isolation on agar plates was repeated 2× more in order to ensure that pure cultures were obtained.

After these selection cycles, 20 individual strains able to grow with L-aspartic acid as sole N source were available.

To test for PPO/Asp transaminase activity, 2 ml cultures of each of the strains were grown as above. Then 400 µl of each of the cultures were permeabilized with 0.5% toluene, 0.5% ethanol at 37° C. for 30 min. The cell pellets were each resuspended in 50 µl of reaction mix consisting of 50 mM PPO, 50 mM L-aspartic acid, 50 mM Tris/HCl, pH=8.0, 10 µM pyridoxal phosphate and incubated at 28° C. overnight.

For qualitative determination of the PPT formed, the reaction supernatants were diluted 1:5 in water and 5 µl portions thereof were analyzed by thin-layer chromatography on cellulose HPTLC plates (Merck) with n-butanol: glacial acetic acid: water=60:15:25 as mobile phase. The amino acids were visualized by ninhydrin staining. It was possible with 4 strains (DSM 13353, DSM 13354, DSM 13355, DSM 13356; all the strains have been deposited at the "Deutsche Sammlung von Mikoorganismen und Zellkulturen GmbH") to detect the formation of phosphinothricin. The enantiomeric purity of the reaction product was by chiral HPLC [investigated with the separation column Chirex® (D) with penicillamine as matrix (manufactured by Phenomenex)] (mobile phase: 2 mM $CuSO_4$, 10% methanol, flow rate: 0.5 ml/min, UV detection: 254 nm, retention times: L-PPT: about 17 min, D-PPT: about 21 min). It was possible thereby to detect L-PPT and no D-PPT as reaction product in all the 4 test samples investigated.

For preparation of L-PPT by biotransformation and a quantitative analysis of the progress of the reaction, 1 l cultures of each of the soil bacterial strains DSM 13354, DSM 13355 and DSM 13356 were grown in the medium as described on page 6 at 28° C. for 48 hours. The cells were harvested by centrifugation, washed 1× in 10 mM NaCl, 10 mM Na phosphate, pH=7.5, and then lyophilized overnight.

To carry out the biotransformation, 200 mg dry biomass of each of the soil bacterial strains identified above were resuspended in 10 ml of the following substrate solution:
100 mM PPO
200 mM L-aspartic acid
100 mM Tris/HCL, pH=8.0
1 mM pyridoxal phosphate The mixtures were incubated on an incubating shaker at 200 rpm and 37° C. 200 µl samples were taken after 1, 2, 4, 8, 24 and 30 h and analyzed in the HPLC as described on page 7. The measured results for L-PPT and L-aspartic acid are summarized in table 1. The maximum conversion rate achieved [produced L-PPT/PPO in the substrate×100] was about 59% (DSM 13355).

TABLE 1

Progress of the PPO/aspartate transamination reaction by biotransformation with soil isolates

| Strain | Reaction time [h]* | L-PPT [mM] | Aspartic acid [mM] |
| --- | --- | --- | --- |
| DSM 13354 | 1 | 3.9 | 174.0 |
|  | 2 | 5.7 | 150.0 |
|  | 4 | 10.3 | 100.0 |
|  | 8 | 23.8 | 30.3 |
|  | 24 | 38.3 | 0 |
|  | 30 | 48.4 | 0 |
| DSM 13355 | 1 | 4.5 | 143.1 |
|  | 2 | 7.7 | 122.7 |
|  | 4 | 11.1 | 98.8 |
|  | 8 | 24.8 | 76.4 |
|  | 24 | 44.9 | 17.2 |
|  | 30 | 59.1 | 9.8 |
| DSM 13356 | 1 | 5.7 | 138.1 |
|  | 2 | 8.4 | 124.4 |
|  | 4 | 12.5 | 95.9 |
|  | 8 | 27.5 | 58.8 |
|  | 24 | 51.3 | 14.3 |
|  | 30 | 49.6 | 7.2 |

*Reaction temperature: 37° C.

2.) Detection of Direct PPO/Aspartate Transamination with Transaminase Enzyme Preparations:

A total of 7 different commercially available transaminases was tested for PPO/aspartate transamination. From microorganisms deriving (thermally stable transaminases AMN-001-01, -001-02, -001-03, -001-04, -001-05, contained in the aminotransferase test kit from Diversa CAT# AMN-001 (1998); glutamate-oxalacetate transaminase (GOT), glutamate-pyruvate transaminase (GPT), Sigma). The enzyme preparations were dissolved with a protein concentration of 5 mg/ml in 50 mM Tris/HCl buffer, pH=8.0, and then dialyzed against the same buffer at 4° C. overnight. This was intended to remove amino donors and acceptors which are possibly present in the enzyme preparations and which might act as intermediate carriers in the transamination. The enzyme solutions were then adjusted to 1 mg/ml and incubated in 50 µl mixtures with reaction buffer consisting of 50 mM PPO, 50 mM L-aspartic acid, 50 mM Tris/HCl, pH=8.0, 10 µM pyridoxal phosphate for 1 h at the temperature optimal for the particular enzyme.

The enzyme tests were analyzed by thin-layer chromatography and chiral HPLC as described in example 1. Enantioselective formation of L-PPT by transamination from L-aspartic acid was detectable with 2 of the thermally stable enzymes, AMN-001-03 and AMN-001-04 (reaction temperature: 80° C.). None of the other enzymes tested showed any reactivity.

3.) Quantitative Investigation of the PPO/Aspartate Transamination with the Thermally Stable Transaminase AMN-001-03:

Because the specific activity was relatively high, the transaminase AMN-001-03 was selected for more accurate characterization of the L-PPT synthesis reaction. 1 ml of a substrate solution consisting of 40 mM PPO, 48 mM L-aspartic acid, 50 mM Tris/HCl, pH=8.0, 0.1 mM pyridoxal phosphate were incubated with 1 mg of AMN-001-03 transaminase at 80° C. To analyze the progress of the reaction, 50 µl aliquots were taken over a period of 24 h and frozen at −20° C. PPT and aspartate were determined in an amino acid analyzer (Biotronic LC 5001). The results are shown in table 2. Under the chosen conditions, the L-PPT synthesis reaction reached equilibrium after 2–4 h. The amino donor employed, L-aspartic acid, was completely consumed after 7 h. A conversion rate [produced L-PPT/PPO in the substrate×100] of about 75% was achieved.

TABLE 2

Progress of the PPO/aspartate transamination reaction with transaminase AMN-001-03

| Reaction time [h]* | L-PPT [mM] | Aspartate [mM] |
| --- | --- | --- |
| 0 | 0 | 53.4 |
| 1 | 9.5 | 47.8 |
| 2 | 20.8 | 33.8 |
| 4 | 25.7 | 12.5 |
| 7 | 29.7 | 0 |
| 24 | 28.1 | 0.4 |

*Reaction temperature: 80° C.

4.) Enzymatic Chiral Synthesis of L-PPT from PPO and Aspartate with Partially Purified Thermally Stable Transaminase AMN-001-03:

Partially purified transaminase AMN-001-03 with a specific activity of 107 nkat/mg of protein (1 nkat=1 nmol of aspartate/sec.) was employed for the synthesis experiments. The reaction solution with a volume of 1 ml contained 552 mM PPO (10%), 700 mM L-aspartic acid, 0.1 mM pyridoxal phosphate, pH=8.0, adjusted with $KHCO_3$, and 11.5 mg of enzyme. The mixture was incubated at 80° C.

Sampling and analysis took place as described in example 3.

The results are compiled in table 3. In this experiment, the reaction equilibrium was reached after only 1 h. The amino donor L-aspartic acid was almost completely consumed after 4 h. The conversion rate was about 52% and the space/time yield was 4.5 of [g of L-PPT/g of biocatalyst/h]. In a parallel experiment with the same substrate solution and enzyme concentration but a reaction temperature of 60° C., a similar conversion rate was achieved although the reaction rate was distinctly reduced. The space/time yield was only 0.95 [g of L-PPT/g of biocatalyst/h]. These results demonstrate the great importance of the high thermal stability of the transaminase for the conversion rate and an efficient reaction procedure. The only moderate conversion rate of 52% is mainly attributable to the formation of the by-product alanine by transamination of pyruvate. Considerably higher conversion rates can be achieved if the production of alanine during the reaction is avoided.

TABLE 3

Preparation of L-PPT by transamination with partially purified thermally stable transaminase AMN-001-03

| Reaction time [h]* | L-PPT [mM] | Aspartate [mM] | Alanine [mM] |
| --- | --- | --- | --- |
| 0 | 0 | 700.0 | 0 |
| 0.5 | 155.3 | 405.8 | 0 |
| 1 | 286.4 | 193.1 | 98.7 |
| 2 | 288.5 | 15.2 | 181.5 |
| 4 | 284.0 | 1.9 | 284.1 |
| 8 | 251.9 | 1.3 | 234.5 |

*Reaction temperature: 80° C.

What is claimed is:

1. A process for preparing L-2-amino-4-(hydroxymethylphosphinyl)butyric acid (L-phosphinothricin, L-PPT) of the formula (I), its derivatives which are selected from the group of carboxylic esters and carboxamides and phosphinic esters and/or its respective salts

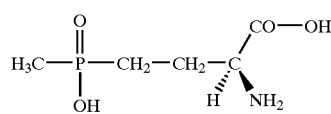

(I)

from 4-(hydroxymethylphosphinyl)-2-oxobutyric acid (HMPB, PPO) of the formula (II)

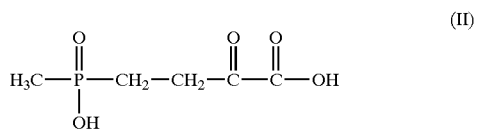

(II)

its derivatives which are selected from the group of carboxylic esters and carboxamides and phosphinic esters and/or its respective salts as acceptor by enzymatic transamination in the presence of aspartate as donor, where the transamination takes place in the presence of one or more acceptor-specific aspartate transaminase(s) (Asp-TA) which transaminase(s) catalyze the direct transfer of the a-amino group from aspartate to 4(hydroxymethylphosphinyl)-2-oxybutyric acid (HMPB, PPO) or its derivatives to give oxaloacetate and the compound of the formula (I), its derivatives and/or salts.

2. The process as claimed in claim 1, wherein the reaction of aspartate as donor and a compound of the formula II, its derivatives which are selected from the group of carboxylic esters and carboxamides and phosphinic esters and/or its respective salts as acceptor takes place in the presence of one or more thermally stable acceptor-specific aspartate transaminases.

3. The process as claimed, in claim 1 wherein the acceptor-specific aspartate transaminases have a low substrate specificity for pyruvate so that the formation of the by-product alanine is avoided as far as possible.

4. The process as claimed in claim 1 wherein one or more of the transaminases are in immobilized form.

5. The process as claimed in claim 1, wherein pyruvate which is present is removed from the reaction mixture by physical, chemical and/or enzymatic means.

6. The process as claimed in claim 4, wherein the conversion of the pyruvate takes place in the presence of one or more acetolactate synthases (ALS) to give acetolactate.

7. The process as claimed in claim 4, wherein the conversion of the pyruvate takes place in the presence of a pyruvate decarboxylase to give acetaldehyde.

8. The process as claimed in claim 4, wherein the conversion of the pyruvate takes place in the presence of a pyruvate oxidase to give acetyl phosphate.

9. The process as claimed in claim 5, wherein the conversion of pyruvate takes place in the presence of a thermally stable enzyme.

* * * * *